United States Patent [19]

Sjönell

[11] Patent Number: 4,572,205

[45] Date of Patent: Feb. 25, 1986

[54] METHOD AT BLOOD PRESSURE MEASUREMENT AND A BLOOD PRESSURE CUFF FOR CARRYING OUT THE METHOD

[76] Inventor: Göran Sjönell, 11 Askrikevägen,, S-181 46 Lidingö, Sweden

[21] Appl. No.: 652,736

[22] Filed: Sep. 21, 1984

[30] Foreign Application Priority Data

Sep. 23, 1983 [SE] Sweden .............................. 8305150

[51] Int. Cl.[4] ............................................... A61B 5/02
[52] U.S. Cl. ..................................... 128/686; 128/327
[58] Field of Search ................ 128/672, 677, 686, 327

[56] References Cited

U.S. PATENT DOCUMENTS

| | | | |
|---|---|---|---|
| 3,812,844 | 5/1974 | Sokol | 128/686 |
| 3,906,937 | 9/1975 | Aronson | 128/686 X |
| 4,210,154 | 7/1980 | Klein | 128/686 X |
| 4,501,280 | 2/1985 | Hood, Jr. | 128/686 X |

Primary Examiner—Lee S. Cohen
Assistant Examiner—Angela D. Sykes
Attorney, Agent, or Firm—Sherman & Shalloway

[57] ABSTRACT

The present invention relates to a blood pressure cuff for measuring slender, normal and thick upper arms as well as thighs. The invention includes a number of sections defining the width of the field acting around the upper arm or thigh at pressure measurement, which sections are connected via a common passageway, having a channel for each section to a force pump creating the pressure, and a throttle means is arranged to connect one or more channels with the air pump depending on the thickness of the arm or thigh.

8 Claims, 5 Drawing Figures

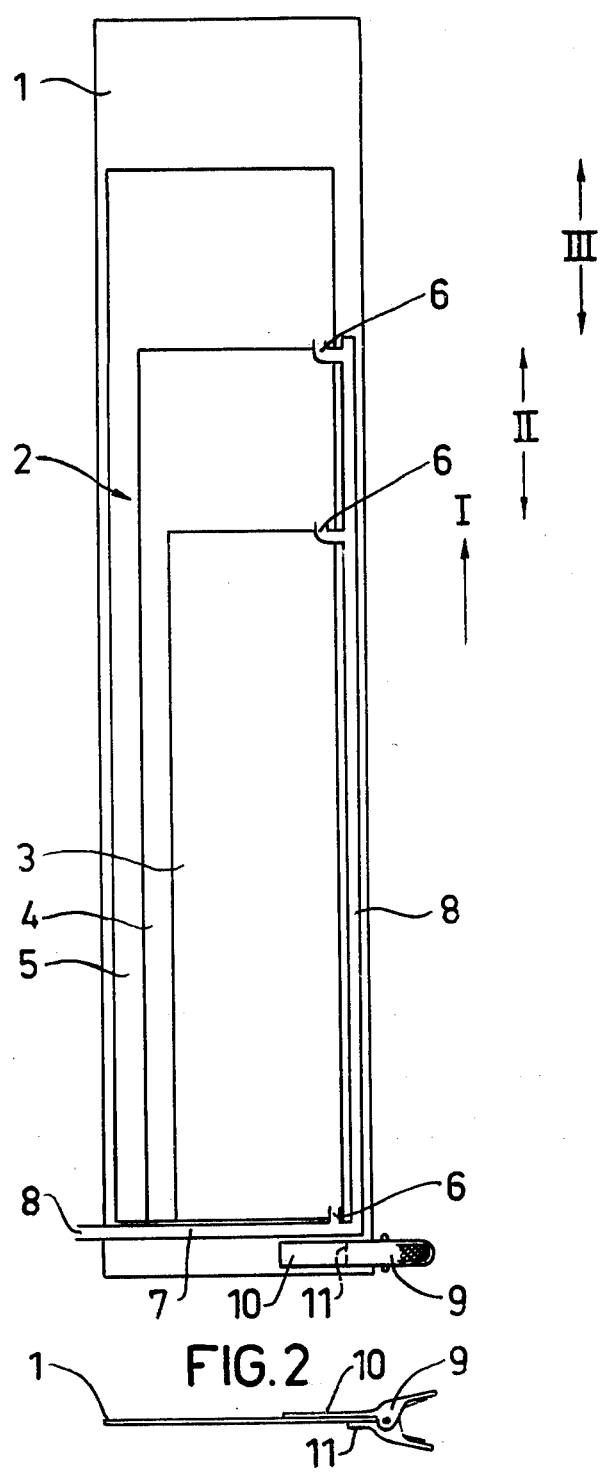

METHOD AT BLOOD PRESSURE MEASUREMENT AND A BLOOD PRESSURE CUFF FOR CARRYING OUT THE METHOD

BACKGROUND OF THE INVENTION

This invention relates to a method of measuring the blood pressure by means of a blood pressure cuff of a new type.

The blood pressure is usually measured by means of a blood pressure cuff which is placed around the patient's upper arm (or sometimes thigh) and which is kept in position by means of a bur fastener. The systolic and diastolic pressure can be measured by the aid of an air pump intended to set the cuff under pressure and a manometer.

Today a standard cuff is used for measuring the blood pressure of all patients independently whether the patient's arm is slender or thick. The width of this standard cuff is about 12 cm. Due to the fact that there is a soft tissue between the blood vessel and the bone in the middle of the arm (or thigh) the real blood pressure measured with the same cuff is ambiguous for different arm thicknesses despite the same read pressure. Thus, a person having a slender arm will have a relatively low read pressure whereas a person having a thick arm will show a relatively high read pressure in spite of the persons in reality having the same blood pressure. In the latter case a higher pressure is required in the cuff to reach, i.e. actuate, the blood vessel. A corresponding lower pressure is required for the slender arm in order to actuate the blood vessel. These conditions mean that the manometer is deflected which means in reality errors to the order of 5-10 mm Hg as to both the systolic and diastolic pressure.

The limit of treating a patient for e.g. increase of blood pressure can be dependent on the fact whether the patient has 95 or 100 in the lower pressure, i.e. the diastolic one. Thus, the error margin of using this standard cuff is many times quite decisive whether a patient is considered as sick or not sick and is to be treated or not.

SUMMARY OF THE INVENTION

This invention tries to solve this problem and adapt the cuff width automatically to the patient's arm thickness (or thigh thickness) in order to eliminate the error margin as far as possible. This is possible by the invention being provided with the characteristic features defined in the claims.

BRIEF DESCRIPTION OF THE DRAWINGS

The blood pressure cuff of the invention will be described more in detail in the form of examples with reerence to the drawing, in which FIG. 1 shows the basic principles of the invention very schematically in the form of a first example, FIG. 2 shows a detail as seen from the side of the cuff according to FIG. 1.

DESCRIPTION OF THE PREFERRED EMBODIMENTS

Figure 3:
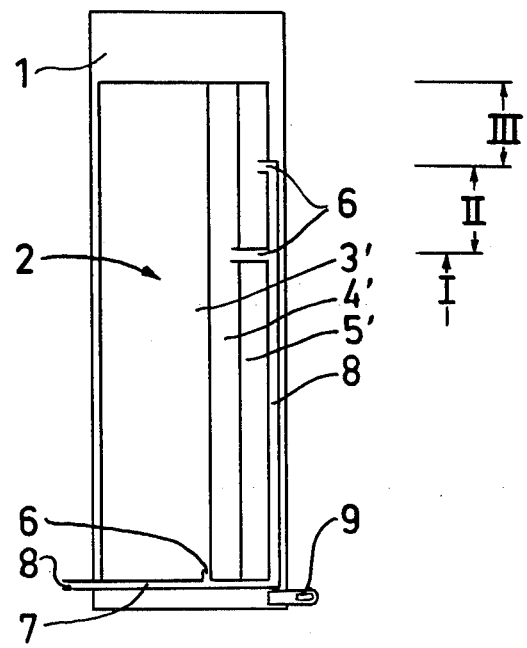
FIG. 3 shows schematically another embodiment of the invention.

In the connection concerned here a conventional cuff with respect to its basic structure with casing, lining and bur fasteners as well as mounted manometer is to be understood by the expression blood pressure cuff, and the cuff is in principle applied in usual manner. The details and components mentioned here are not shown more closely on the drawing or described in the following because they are no part of the invention.

On the drawing 1 designates a supporting frame or lining carrying the pressure creating part or parts of the pressure cuff which is the essential difference as compared with known blood pressure cuffs. 2 generally designates the cushion or bladder acting for the pressure measurement. This bladder 2 is divided into secondary bladders or sections 3, 4 and 5, see FIGS. 1 and 4. A channel 6 leads to each section via a flexible line 7 connected to a manometer and air pump (not shown).

Figure 4:
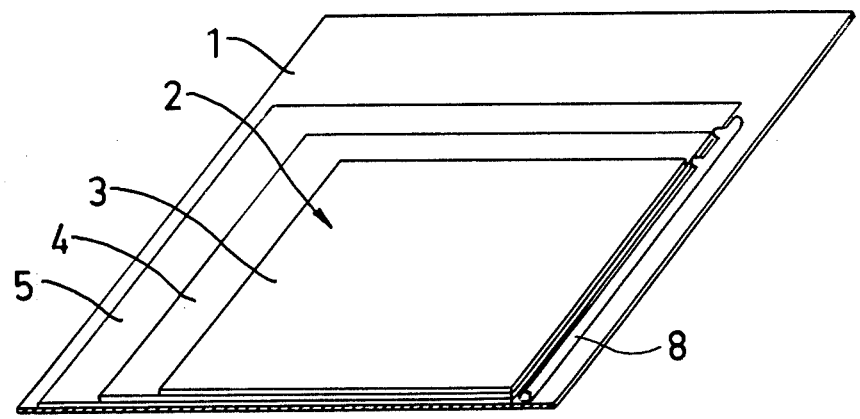
FIG. 4 shows a sectional perspective view of the embodiment according to FIG. 1

The bladder 2 shown in FIGS. 1 and 4 consists of three sections of different width and length starting from a common end edge of the cuff. The secondary bladders or sections 3-5 can either, as shown in FIG. 4, be made each in one piece and placed above each other or, as shown in FIG. 5, be formed by glueing, vulcanizing or welding a bladder corresponding to the section 5 along lines so that the three sections shown in FIG. 1 are obtained.

Figure 5:
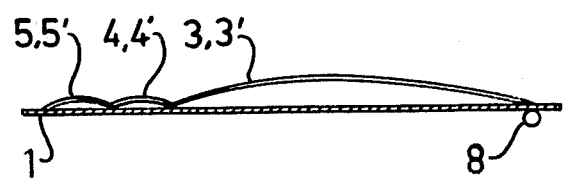
FIG. 5 shows schematically a section of the embodiment according to FIG. 3 in a somewhat modified form.

According to FIG. 3 the bladder 2 consists of three secondary bladders or sections 3', 4' and 5' of equal length, the bladder 2 thus being formed either by three separate secondary bladders of sections 3'-5', or else one single bladder can be glued, vulcanized or welded, as previously described, along two lines to form the secondary bladders shown, cf. FIG. 5. Also these sections 3'-5' start from one common end edge of the cuff.

Common to the embodiments shown here is that the flexible line 7 connecting the channels 5 extends substantially parallelly to one longitudinal edge of the cuff, which part of the line is designated 8. A clip 9 is attached with one of its legs 10 in the frame of the pressure cuff and in connection with the end edge common to the sections.

Using the blood pressure cuff of the invention the cuff is applied in usual manner around e.g. a patient's upper arm. Has the patient an arm of a normal size said end edge will be applied within the range II, see FIGS. 1 and 3. The clip 9 is made to grip with its free leg 11 the part of the cuff lying above and will then squeeze together and throttle the channel 8 on one place within the range II. This means that the section 5 will not obtain any compressed air when the cuff is pumped up. Only the sections 3 and 4 will act, the width of the section 4 being adapted to normal arms, that is to say, the "free" length 11 of the section 4 will correspond to a circumferential range covering the designation "normal arms". If the patient has a slender arm the clip 9 will in a corresponding way be applied inside the range I, the flexible line portion 8 being throttled so that compressed air will not have access to the sections 4 and 5 but only to the section 3. The width of the latter is adapted to normal arms whereby it is to be understood also here that the length of the section 3 corresponds to the maximum circumference which can be referred to "slender arms". If the cuff is applied around a thick arm the clip 9 will be placed in the range III, i.e. the clip 9 will not block the line portion 8. This means that all the sections can be filled with compressed air, whereby it is appreciated that the section 5 has a width adapted to thick arms.

The total sectional width of slender arms can e.g. lie between 8 and 11 cm, for normal arms about 12 cm and for thick arms e.g. about 14–15 cm. This is only examples and it is to be understood that more than three sections can be used within the scope of the invention, by which it is possible to obtain an additional exactness at blood pressure measurement of different arm thicknesses with the same cuff.

In FIG. 5 the flexible line portion 8 is shown as placed on the other side of the supporting frame 1, as compared with FIGS. 1, 3 and 4. This will only show that the invention is of course not restricted as to the exact location of the line portion 8 and the secondary bladders or sections can of course be displaced relative to each other provided the criteria intended for the invention are fulfilled. The illustrative examples described here and shown on the drawing are only intended to clarify simple, cheap and practical embodiments of the inventive idea.

The clip described to achieve a practical solution of the throttling of the line 8 can be replaced with other means within the scope of the invention and the knowledge of one skilled in the art, but the throttling point must be within the intended area.

Despite the fact that the invention has substantially been described in connection with blood pressure measurement of upper arms it is to be understood that the invention can also be dimensioned for measurement of the thighs.

I claim:

1. A blood pressure cuff for attachment to a body limb, comprising
   (a) a support having bladder means for applying pressure to said body limb, said bladder means including a plurality of chambers each said chamber having unique dimensions;
   (b) air pump means for inflating said bladder means;
   (c) passageway means for fluidly connecting said air pump means with said bladder means, said passageway means including a main passage and a branch passage for each said chamber, each said branch passage connecting said main passage with a respective said chamber;
   (d) clip means associated with said support for selectively occluding said passageway means, said support being adapted to be attached to said limb in surrounding relation thereto with said clip means being engaged with said support to aid in the retention of said support on said limb, said clip means when so engaged occluding said passageway means at a location thereon dependent upon the size of said limb, whereby only any branch passage or passages between said clip means and said air pump means receive air during operation of said air pump means.

2. The invention of claim 1, wherein said clip means is attached to one end of said support.

3. The invention of claim 2, wherein said support is elongated in a direction away from said one end and has two sides in the direction of said elongation at least a first portion of said passageway means being located along one of said sides.

4. The invention of claim 3, wherein said passageway means includes a second portion thereof extending along said one end.

5. The invention of claim 4, wherein a first said branch passage is located in said passageway means second portion and a second said branch passage is located in said passageway means first portion.

6. The invention of claim 1, wherein said bladder means includes three said chambers, a first chamber having dimensions suited for engagement on a slender limb, and a second and third respective chambers having dimensions suited for respective medium-sized and large-sized limbs.

7. The invention of claim 1, wherein said bladder means includes three chambers, a first main chamber having dimensions sized for engagement on a slender limb, a second chamber which when inflated with said first main chamber combines therewith to form a composite bladder sized for engagement on a medium-sized limb, and a third chamber which when inflated with said first main chamber and second chamber combines therewith to form a further compositie bladder sized for engagement on a large-sized limb.

8. A method of measuring blood pressure comprising the steps of:
   (1) providing a blood pressure cuff comprising:
      (a) a support having bladder means for applying pressure to a body limb, said bladder means including a plurality of chambers each said chamber having unique dimensions;
      (b) air pump means for inflating said bladder means;
      (c) passageway means for fluidly connecting said air pump means with said bladder means, said passageway means including a main passage and a branch passage for each said chamber, each said branch passage connecting said main passage with a respective said chamber;
      (d) clip means associated with said support for selectively occluding said passageway means;
   (2) encircling said limb with said support;
   (3) engaging said support with said clip means to retain said support on said limb, the location of engagement of said clip means with said support being dependent upon the size of said limb;
   (4) occluding said passageway means with said clip means to thereby isolate any branch passage or passages downstream of the location of said occluding, from said air pump means;
   (5) activating said air pump means to inflate said bladder means; and
   (6) measuring said blood pressure.

* * * * *